United States Patent [19]

Simon et al.

[11] Patent Number: 4,783,496

[45] Date of Patent: Nov. 8, 1988

[54] SHAPED BODIES OF PLASTIC MATERIAL HAVING HIGH ELASTICITY AND HIGH ADHESIVE CHARACTERISTICS

[75] Inventors: Wilhelm Simon, Zollikon; Urs Oesch, Uster, both of Switzerland

[73] Assignee: Willi Möller, Zürich, Switzerland

[21] Appl. No.: 914,390

[22] Filed: Oct. 2, 1986

[30] Foreign Application Priority Data

Oct. 4, 1985 [CH] Switzerland ................. 4306/85

[51] Int. Cl.$^4$ .................. C08K 5/09; C08L 27/00; C08F 10/00
[52] U.S. Cl. .................. 524/292; 524/293; 524/569; 526/284
[58] Field of Search .............. 526/284; 524/293, 569, 524/292

[56] References Cited

U.S. PATENT DOCUMENTS

| | | | |
|---|---|---|---|
| 3,332,964 | 7/1967 | McCracken et al. | 560/89 |
| 3,389,168 | 6/1968 | Hirzy | 260/485 |
| 4,309,524 | 1/1982 | Huemner et al. | 526/284 |
| 4,608,149 | 8/1986 | Daniel et al. | 204/418 |

FOREIGN PATENT DOCUMENTS 59-074144 4/1984 Japan .

*Primary Examiner*—Joseph L. Schofer
*Assistant Examiner*—N. Sarofim
*Attorney, Agent, or Firm*—Seidel, Gonda, Lavorgna & Monaco

[57] ABSTRACT

Shaped bodies of plastic material have a high elasticity and high adhesive characteristics if they contain, referred to the percentage of the plastic material of said shaped bodies, a higher percentage of a benzophenone-tetracarboxylic acid tetraester. In said benzophenone-tetracartoxylate the ester forming alcohol component is an alkanol, alkenol or alkynol having 4–24 carbon atoms. The shaped bodies can be adhered to a substrate by pressing them onto it. The inventive shaped bodies are preferably strands, fibers, filaments or foils, for example foils for the packaging of products. Preferred shaped bodies are ion sensitive membranes for the determination of the concentration of ions and said membranes contain furthermore an ion selective component for the ion to be determined.

Solutions of the inventive shaped bodies in a volatile organic solvent can be applied to a substrated and after the solvent is evaporated there remains on the substrate a firmly adherent elastic film.

19 Claims, No Drawings

SHAPED BODIES OF PLASTIC MATERIAL HAVING HIGH ELASTICITY AND HIGH ADHESIVE CHARACTERISTICS

BACKGROUND OF THE INVENTION

This invention is concerned with shaped bodies of plastic material having a high elasticity and high adhesive characteristics. Said shaped bodies, like e.g. foils, can be firmly adhered to a substrate, like e.g. a silicon containing substrate, due to their good adhesion. Said shaped bodies contain high quantities of a benzophenonetetracarboxylic acid tetraester as a elastifying component, usually 15–90 parts by weight of said elastifying component per 10 parts by weight of the plastic material. The highly elastic shaped bodies can e.g. be ion selective membranes which contain as further component an ion selective substance.

DESCRIPTION OF THE PRIOR ART

It is well known in the art to add to the plastic material plasticizers in order to make plastic materials which are brittle or not sufficiently flexible usable in any field of application.

Furthermore, ion selective membranes for the determination of the concentration of several cations are well known in the art. Said ion selective membranes contain a component which is ion selective for the cation to be determined in a matrix of plastic material. Usually said ion selective membranes, furthermore, contain a plasticizer which furthermore increases the selectivity of the membranes for the ion to be determined and which, furthermore, enhances the stability of ion selective electrodes which are equipped with such an ion selective membrane.

Typical examples plasticizers which were used until now ion selective membranes are esters of dicarboxylic acids like e.g. esters of the phthalic acid, of the sebacic acid or the adipic acid and, furthermore, aromatic ethers, aliphatic ethers and esters of the phosphoric acid, like e.g. mixed aromatic and aliphatic phosphoric acid esters.

In the Japanese patent publication Nos. 17 851/1982 and 17 852/1982 of Fuji which were published on Jan. 29, 1982, there are described electrodes which are sensitive for potassium ions and which contain as ion sensitive component valinomycine, as polymer matrix polyvinylchloride and as plasticizer dioctylphthalate.

In the European patent publication No. 0 129 233 of Eastman Kodak Company there are as well described membranes sensitive for potassium ions which contain as ion sensitive component valinomycine, as plastic matrix a preferably hydrophobic polymeric material like e.g. a copolymer of vinylchloride and vinylacetate and as plasticizer a diester of a dicarboxylic acid having at least 25 carbon atoms and a viscosity at a temperature of 20° C. of less than 120 centipoise, and furthermore a boiling point of more than 170° C. at a pressure of 5 mm Hg. Said plasticizer is present in such an amount that the valinomycine is dissolved therein and a 100%–500% excess of said plasticizer can be present. A preferred plasticizer used in said membranes is the diisodecylphthalate.

In the U.S. Pat. No. 3 389 168 of J. W. Hirzy there are described diallyl-benzophenone-tetracarboxylates having the formula

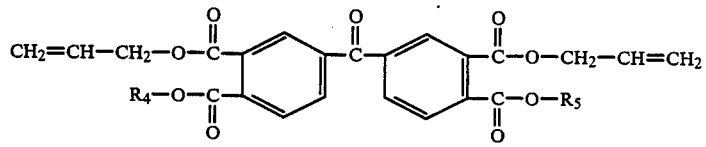

wherein $R_4$ and $R_5$ are selected from the group comprising allyl, alkyl having 1–18 carbon atoms and cycloalkyl having 6–18 carbon atoms. Said benzophenone tetracarboxylates are used as plasticizers and crosslinking agents for halogen containing vinyl polymers and according to the examples 16 and 17 of said patent per 100 parts by weight of polyvinylchloride 60 parts by weight of said plasticizer are used.

In the Japanese patent publication No. 59-74,144 of Kokai Tokkyo Koho and in the corresponding patent abstracts of Japan, volume 8, number 178 (C-338) [1615], Aug. 6, 1984, there are described plasticizers for vinylchloridepolymeres which have the following formula A

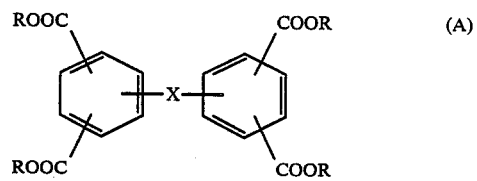

In said formula A R is an aliphatic saturated hydrocarbon residue having 4–18 carbon atoms, X is oxygen, sulphur or a group of formula

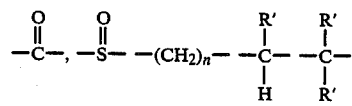

wherein n is 1–6 and R' is a methyl group or trifluoromethyl group, or X has the meaning of certain bivalent organic residues which are bonded via an ether group to the two benzene nuclei. Per 100 parts by weight of vinylchloride resin 20–120 parts by weight, preferably 30–100 parts by weight of said tetracarboxylic acid tetraester of formula A are used. The plastified polyvinylchloride is advantageous for the preparation of bags in which blood can be stored, because the plasticizer does not migrate from the plasticized plastic material into the stored blood. From said Japanese patent publication no reference can be taken that the plasticized polyvinylchloride resins have a good adherence and a high elasticity.

DETAILED DESCRIPTION OF THE INVENTION

It was now quite unexpectedly found out that benzophenonetetracarboxylic acid tetraesters and among said esters also such which correspond to the esters of formula A of the Japanese patent publication, if in said esters X is the group —CO—, can be used to prepare shaped bodies of plastic material having a high elasticity and high adhesive characteristics, provided that said benzophenonetetracarboxylic acid tetraesters are used in far higher quantities than the quantities in which plasticizers are usually used in order to plasticize plastic materials.

One object of the present invention, accordingly, is a shaped body of plastic material having a high elasticity and high adhesive characteristics which shaped body contains per 10 parts by weight of a plastic material 7 parts by weight to 90 parts by weight of an elastifying component which is a benzophenonetetracarboxylic acid tetraester, in which the ester forming alcohol component is selected from the group comprising alkanols having 4–24 carbon atoms, alkenols having 4–24 carbon atoms and alkynols having 4–24 carbon atoms and wherein in said benzophenonetetracarboxylates there are optionally present in the phenyl nuclei or in the residues of the alcohol component non ionic substituents, with the provision that if the plastic component of said shaped body contains a vinylchloridehomopolymer or vinylchloridecopolymer or consists of said homopolymers or copolymers, there have to be present per 10 parts by weight of said plastic material at least 12 parts by weight of the benzophenonetetracarboxylate.

Preferred benzophenonetetracarboxylates used as plastifying component in the inventive shaped bodies of plastic materials are corresponding tetraesters, in which the alcohol component is a straight chain alcohol or a branched alcohol having a single branch only which extends from the straight main chain. Furthermore, preferably in the benzophenonetetracarboxylic acid tetraesters to each of the two benzene nuclei there are bonded two ester groups. Furthermore, preferably the position of the two ester groups, referred to the carbon atoms of the benzene nucleus to which the carbonyl group of the benzophenone is bonded, is identical in each of the two benzene nuclei.

Preferred such benzophenonetetracarboxylates have the following formula I

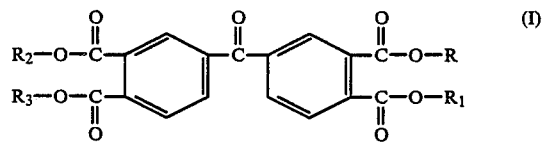

in which formula the radicals R, $R_1$, $R_2$ and $R_3$ are selected from the group comprising alkyl radicals having 4–22 carbon atoms, alkenyl radicals having 4–22 carbon atoms and alkinyl radicals having 4–22 carbon atoms, and said radicals are preferably straight chain radicals or branched chain radicals in which only a single branch extends from the main chain.

In the benzophenonetetracarboxylates of formula I the radicals R, $R_1$, $R_2$ and $R_3$ are preferably alkyl radicals having 6–20 carbon atoms, alkenyl radicals having 6–20 carbon atoms or alkinyl radicals having 6–20 carbon atoms.

Benzophenonetetracarboxylates having a symmetrical structure are preferred, i.e. corresponding esters in which the alcohol component of the four ester groups is identical. Said symmetrical esters, furthermore, are easier to be synthesized than esters in which the four alcohol components of the four ester groups are different from each other. Accordingly those benzophenonetetracarboxylates of formula I are preferred, in which the four radicals R, $R_1$, $R_2$ and $R_3$ are identical and preferably straight chain alkyl groups having 6–20 carbon atoms.

The plastic component of the inventive shaped bodies is preferably a plastic material having hydrophobic properties. Examples for such plastic materials are polyethylene, polypropylene, polyvinylhalide, polystyrene, polyesters, polyamides, polyacrylnitrile, polymethacrylnitrile, polyurethanes, polycarbonates, polyvinylidenehalides and such cellulosic derivatives which have a relatively high hydrophobicity and, furthermore, copolymers containing two or more of monomeric units. Copolymers optionally can also contain smaller quantities of monomeric units having more hydrophilic properties like e.g. monomeric units which have hydrophylic substituents like hydroxy groups, lower aliphatic ethers, ester groups and optionally even some carboxylic acid groups. Examples for monomeric units having higher hydrophilic properties which can be contained in corresponding copolymers are vinyl alcohol and vinyl acetate.

The monomeric units of the polymeric material can comprise any desired hydrophobic substituents like e.g. alkyl groups if for example vinyltoluene is the monomeric material of a homopolymer or a monomer component of a corresponding copolymer.

In the inventive shaped bodies the polymeric materials can furthermore comprise in their structure unsaturated groups and for instance in the polymeric chain there can be present alkine groups or alkene groups which unsaturated groups are present in the polymeric chain if monomeric components are used which have in their structure two unsaturated groups like e.g. dienes as for example butadiene.

The vinyl halides respectively vinylidene halides used as monomer components for the preparation of corresponding homopolymers or copolymers can be for example vinyl-bromides, vinylidene-bromides, vinylfluorides or vinylidene-fluorides. Preferably, however, the corresponding vinyl halides respectively vinylidene halides are the chlorides.

A preferred plastic material of the inventive shaped bodies is a polymeric material which contains a vinylchloridehomopolymer or vinylchloridecopolymer or consists of said polymers.

As already outlined before it is essential that in this case there are present in the shaped bodies per 10 parts by weight of the vinylchloridehomopolymer or vinylchloridecopolymer at least 12 parts by weight of the benzophenonetetracarboxylate. Preferably the shaped bodies contain per 10 parts by weight of the polyvinylchloride 15–90 parts by weight and specially preferred 20–70 parts by weight of the benzophenonetetracarboxylate.

It is essential that the shaped bodies have such high contents of the elastifying component. If a shaped body of a vinylchloridehomopolymer or vinylchloridecopolymer contains per 10 parts by weight of said plastic material less than 12 parts by weight of the benzophenonetetracarboxylate or if a shaped body of any other plastic material contains per 10 parts by weight of the plastic material less than 7 parts by weight of the elastifying benzophenonetetracarboxylate, then the benzophenonetetracarboxylate acts only as plasticizer in said shaped bodies, however the corresponding shaped bodies do not have the intended high elasticity and the high adhesive properties which are necessary in order to ensure a good adherence of the shaped bodies onto different substrates like substrates containing silicon like e.g. glass substrates, substrates of silicondioxide, substrates of silicone material and substrates containing $Si_3N_4$ or consisting of $Si_3N_4$.

Usually the inventive shaped bodies contain per 10 parts by weight of the plastic material 15-80 parts by weight of the benzophenonetetracarboxylate. Specially preferred are shaped bodies which contain per 10 parts by weight of the polymeric material 20-70 parts by weight of the benzophenonetetracarboxylate.

If the plastic material of the inventive shaped bodies is a vinylchloridehomopolymer or vinylchloridecopolymer, then the best results as to the adhesive characteristics of the shaped body and as to the elasticity, are achieved if the shaped body contains per 10 parts by weight of said plastic material 20-30 parts by weight of the benzophenonetetracarboxylate. For example a shaped body containing 30% by weight of polyvinylchloride plus 70% by weight of the benzophenonetetracartoxylate is highly elastic and adheres well to different kinds of substrates, including the silicon containing substrates mentioned above.

Inventive shaped bodies which contain per 10 parts by weight of the plastic material more than 90 parts by weight of the benzophenonetetracarboxylates usually have an insufficient stability of the shape at room temperature or at temperatures slightly above room temperature like e.g. a temperature of 40° C. The shaped bodies then begin to flow. Accordingly considerations as to the stability of the shape determinate the maximum content of the benzophenonetetracarboxylate in the inventive shaped bodies and said maximum content depends also from the special plastic material present in said shaped bodies so that in several cases per 10 parts by weight of the plastic material not more than 70-80 parts by weight of the benzophenonetetracarboxylate should be used.

An essential advantage of the benzophenonetetracarboxylates present in the inventive shaped bodies over plasticizers which usually are used in plastic materials, like diesters of dicarboxylic acids, like phthalic acid, sebacic acid and adipic acid, as well as esters of phosphoric acids, is the drastically reduced migration of the benzophenonetetracarboxylate in the matrix of the plastic material. Said reduced migration of the benzophenonetetracarboxylates in the matrix of the plastic material results in that said benzophenonetetracarboxylate is not washed out from the plastic material if it is in contact with solvent systems like e.g. aqueous solvent systems. Corresponding tests which were performed with benzophenonetetracarboxylates in which the esterifying alcohol component comprises 9-15 carbon atoms showed that said elastifying component is not leached out from the plastic material if a corresponding membrane containing 30 parts by weight of polyvinylchloride plus 70 parts by weight of the benzophenonetetracarboxylate, is contacted with an albumine solution during several days. Contrary to this a corresponding shaped body which contains instead of the benzophenonetetracarboxylate a corresponding ester of the sebacic acid lost under the same conditions 90% of the originally present sebacate plasticizer.

The fact that the elastifying component of the inventive shaped bodies is not leached out or washed out by any liquid materials, like e.g. aqueous solutions, is very important if the inventive shaped bodies are used in a field of application where they are in frequent contact with liquids. Inventive shaped bodies having the form of a film or a foil are well suited for packing humid products like e.g. foodstuff. Furthermore, inventive shaped bodies having the shape of strands, filaments or fibers, can be advantageously used in such fields of application where said products frequently come into contact with liquid media, like e.g. aqueous media.

Accordingly, the inventive shaped bodies preferably have the form of a foil, or a film, a fiber, a strand or a filament.

According to a preferred embodiment of the present invention the inventive shaped body is an ion sensitive membrane for the determination of the concentration of ions. Said ion sensitive membrane contains as further component an ion sensitive component for the determination of the cation or anion in question. As already outlined above the benzophenonetetracarboxylates are not leached out of such membranes if they are frequently in contact with aqueous media, like e.g. with body fluids if such ion sensitive membranes are used in the clinical field. The ion sensitive membranes which contain the benzophenonetetracarboxylate as elastifying components, accordingly, have a highly extended life time compared with corresponding ion sensitive membranes which contain any of the other plastifiers used until now in such membranes, like e.g. the esters of dicarboxylic acids.

Preferred inventiveion sensitive membranes comprise 10 parts by weight of polyvinylchloride, 15-90 parts by weight, preferably 20-70 parts by weight, of the benzophenonetetracarboxylate and 0,1-1 parts by weight of the ion selective components.

A further object of the present invention is the use of the inventive shaped bodies for adhering said shaped body to a substrate wherein the shaped body having high adhesive characteristics and high elasticity is adhered to the substrate by pressing it onto the substrate or wherein the shaped body is dissolved in a solvent, said solution applied to the substrate and thereafter the solvent evaporated so that a layer of the highly elastic plastic material remains adhered to the substrate.

The substrate can be coated with a layer of a highly elastic inventive shaped body by applying a foil of said highly elastic shaped body having adhesive characteristics onto the substrate and wherein said foil is applied to the substrate either not elongated or after it had been stretched or elongated and wherein the adhesive characteristics of the applied foil ensure a permanent adhesion of said foil onto the substrate.

According to a further embodiment, however, the substrate can be coated with a layer of a highly elastic inventive shaped body by preparing a solution of the shaped body in a volatile solvent, applying said solution onto the substrate, evaporating thereafter the solvent from said solution so that there remains on the substrate a firmly adhered layer of the shaped body having high elasticity.

Inventive shaped bodies having the shape of a cube or a flat cylinder can be simply fixed onto the substrate by pressing them to the substrate. It is furthermore possible to use the inventive shaped bodies in order to fix a first substrate onto a second substrate. In this case the shaped body is first fixed on the first substrate by pressing it onto it and then onto said shaped body fixed on the first substrate there is pressed the second substrate so that the first substrate is fastened onto the second substrate via the inventive shaped body. The inventive shaped bodies accordingly can be used for fastening products like sheets of paper, web materials or plastic materials onto substrates like wood, metal, glass, painted walls, tapestry or similar materials.

Preferred inventive shaped bodies have the form of an elastic foil or an elastic sheet. It is possible to produce thin inventive foils by casting a solution which contains the plastic material and the elastifying benzophenonetetracarboxylate. For example a solution of 10 parts by weight of polyvinylchloride and 30 parts by weight of benzophenonetetracarboxylate in a sufficient amount of a volatile organic solvent, for example tetrahydrofurane, can be cast applying standard solvent casting techniques yielding inventive foils having thicknesses of 3 $\mu m$–200 $\mu m$. Said foils are very tacky, have a high elasticity and a good adhesion to several substrates like silicon containing substrates or substrates of plastic materials, like poly(methylmetacrylate).

Inventive shaped bodies which are sheets or foils have a high elasticity and furthermore good mechanical properties, specially a high tensile strength and high breaking strain. Said elastic plastic foils can be applied to a substrate while being not stretched or extended. They adhere firmly to the substrate to which they are applied. It, however, is also possible to apply such plastic foils onto the surface of a substrate after they had previously been extended or stretched. As soon as no stretching force is exerted onto said foil, the resiliency respectively the restoring force provide a still improved adherency of the foil on the substrate. Foils which are applied to a substrate while being not stretched and also foils being applied to a substrate while being stretched, have a permanent and good adherence onto said substrate.

It furthermore is possible to dissolve an inventive shaped body in a volatile organic solvent and to apply said solution onto a substrate, e.g. by painting it onto the substrate, spraying it onto the substrate or casting it onto the substrate. As soon as the volatile solvent is evaporated there remains on the substrate a firmly adherent film of the elastified plastic.

Inventive plastic foils and sheets and films of the inventive elastified plastic which had been applied to a substrate using a suitable solvent can be used for different packaging purposes. If said films or foils are in direct contact with an aqueous medium, for instance with a humid foodstuff or liquid foodstuff or beverage, then it is advantageous that the elastifying benzophenonetetracarboxylate does not migrate from said foil or film into the foodstuff or beverage even after long periods of storage. Inventive plastic foils can also be used for adhering a material which itself has no adhesive property onto a substrate like e.g. a substrate of glass, paper or plastic. In this case, onto the corresponding substrate there is first applied a material having no adhseive properties, like e.g. a non adhesive sheet, and over said non adhesive sheet a greater area than the are of the non-adhesive sheet material of an inventive adhesive foil is applied, for instance a corresponding inventive foil which had previously been extended or stretched. In those areas where the inventive adhesive foil comes into direct contact with the substrate, said foil adheres to the substrate. In those areas where the inventive adhesive foil comes into contact with the not-adhesive sheet material, the inventive adhesive foil adheres to it and presses it in direction to the substrate. Thereby the non-adhesive sheet material is firmly fixed on the substrate. For instance the non-adhesive sheet material can be a printed paper sheet and so in a single packing step the product is described or labelled and packed. Of further advantages in the field of packaging is, that small molecules like oxygen or carbon dioxide are able to pass inventive foils.

Preferred inventive shaped bodies are ion sensitive membranes for the determination of concentration of ions, like e.g. cations. Such membranes contain, as outlined before, in addition to the plastic material and the benzophenonetetracarboxylate an ion selective component which has a selectivity for the ion to be determined. Many of such ion selective components are described in the literature and is referred for example to what is stated in the U.S. Pat. No. 2,957,607. In such ion selective membranes the ion selective component is usually completely dissolved in the plasticizer of said ion selective membranes.

As already outlined before the plasticizers used in such ion selective membranes until now were certain ethers, the esters of dicarboxylic acids and of phosphoric acids. It was now quite unexpectedly found out that the elastifying component of the inventive shaped bodies, i.e. benzophenonetetracarboxylates, results in many unexpected advantages if the inventive shaped bodies are such ion selective membranes and if said benzophenonetetracarboxylate substitutes in said membrane the prior art plasticizers used in said field of application.

As already outlined before each of the four alcohol moieties of the benzophenonetetracarboxylates has to have 4–24 carbon atoms, preferably 6–20 carbon atoms and specially preferred 9–15 carbon atoms, and furthermore said alcohol moieties are preferably derived from straight chain alcohols. Accordingly, said long aliphatic chains of the inventive benzophenonetetracarboxylates make said substances lipophilic and said long aliphatic chains furthermore also decrease the dynamic viscosity of said benzophenonetetracarboxylates due to the large molar mass of said substances and due to interactions between the long aliphatic chains. Said long aliphatic chains furthermore provide the drastically reduced mobility of the benzophenonetetracarboxylate in the polymer matrix of the plastic component due to entanglements of said long aliphatic chains with the polymer chains. In corresponding ion sensitive membranes, however, said entanglements obviously also drastically reduce the mobility of the ion sensitive component in said system of polymer matrix plus benzophenonetetracarboxylate plus ion sensitive components. Corresponding tests were performed with membranes containing as ion sensitive component the N,N'-bis[(11-ethoxycarbonyl)undecyl]N,N'-dimethyl-2,3-naphtalenedioxydiacetamide, which is described in the publication of D. Ammann, R. Bissig, M. Güggi, E. Pretsch, W. Simon, I. J. Borowitz and L. Weiss in Helv. Chim. Acta 58 (1975) 1535. In corresponding membranes, having a polyvinylchloride polymer matrix in which said ion sensitive component is present, the mobility of said ion sensitive component is drastically decreased if a benzophenonetetracarboxylate is used as elastifying component of such membranes, compared with corresponding membranes for comparison in which the same ion sensitive component is used in a polyvinylchloride polymer matrix, however in combination with the prior art plasticizer bis(2-ethyl hexyl) sebacate. Ion sensitive electrodes equipped with corresponding ion sensitive membranes were as well tested and it was found out that the life period of the electrode in which the above stated inventive ion selective membrane was used was about the tenfold of the life period of the electrode which has been equipped with the above stated ion selectrive membrane for comparison.

The drastically reduced mobility of the ion sensitive component in such ion sensitive membranes is particularly attractive in respect to miniaturized multi ion sensing system, wherein sensing areas which are sensitive for different kinds of ions will be arrayed in closed proximity. Using the benzophenonetetracarboxylates as elastifying components of such multi ion sentizing systems a cross contamination of laterally diffusing different ion sensitive components within different areas of the membrane coating on the top of such a sensor array is almost inhibited.

It is furthermore important that the diffusion of small molecules, such as carbon dioxide, is possible through corresponding ion sensitive membranes containing the benzophenone tetracarboxylate as elastifying components. This makes it possible to prepare corresponding ion sensitive membranes which contain an ion sensitive component which makes possible the determination of carbon dioxide, like e.g. the ion sensitive component described in the publication of J. W. Ross, J. H. Riseman and J. A. Krueger in Pure Appl. Chem 36 (1973) 473: "Potentiometric gas sensing electrodes". Furthermore also corresponding ion sensitive membranes can be prepared in which the ion sensitive component is sensitive for bicarbonate ions, like e.g. ion sensitive components which will soon be described in the publication of U. Oesch, E. Malinowska, W. Simon, (1986) "High speed bicarbonate-selective electrode based on planar thin membrane technology" which is still in preparation. Also bicarbonate anions diffuse fast enough through corresponding ion sensitive membranes in order to enable a sensitive determination of said anion. The same is also true for oxygen and accordingly also ion sensitive membranes for the determination of oxygen, like e.g. in body fluids, can be prepared which contain a corresponding ion sensitive component enabling the determination of oxygen and furthermore a polymer matrix and the benzophenonetetracarboxylates as plastifying component.

A further advantage of inventive shaped bodies which are ion sensitive membranes for the determination of cations and anions and which contain as further component the ion sensitive constituent is, that such membranes can be easily applied to electrode bodies in order to produce ion sensitive electrodes equipped with such an ion sensitive membrane. Examples for electrode bodies which can be used are electrode bodies of glass or of silanizated glass. Due to the high adhesive characteristics of corresponding inventive membranes said membranes adhere firmly onto the electrode body and they are not removed from the electrode body by rubbing with the finger. When said electrodes equipped with the inventive ion sensitive membranes are contacted with a liquid medium in order to determinate therein the concentration of cations or anions, then the plastic foil adheres firmly onto the electrode body and is not removed by said liquid medium.

The following examples shall further illustrate the present invention, they however can in no way be regarded as limitative.

EXAMPLE 1

Preparation of a benzophenonetetracarboxylic acid tetraester

The present example illustrates the preparation of a benzophenonetetracarboxylate having the following formula I

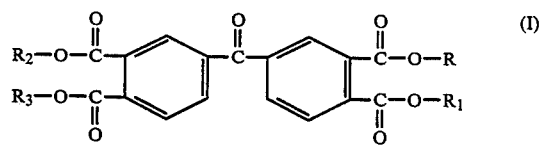

in which formula each of the radicals R, $R_1$, $R_2$ and $R_3$ is a straight chain alkyl radical having 11 carbon atoms.

To a solution of 5 g (0,0155 mol) of 3,3',4,4'-benzophenone-tetracarboxylic acid dianhydride, 10,96 g (0,0636 mol) of undecane-1-ol in 100 ml of toluene, there is added 1 g of sulphuric acid. The sulphuric acid had been previously dissolved in 5 ml of toluene and is added while stirring the solution at room temperature. As soon as the complete amount of sulphuric acid had been added, the mixture is refluxed for four hours while the water which was split off during the esterification reaction was removed via the refluxing column.

Thereafter the solvent was evaporated, the residue dissolved in chloroform and the organic layer was washed with water and twice with a 10% aqueous solution of sodium bicarbonate.

After the evaporation of the chloroform 13,8 g of the crude benzophenonetetracarboxylate remained, corresponding to a yield of 91% of the theoretical yield. Said crude product was purified by flash-chromatography (35 k Pa) on a column filled with silicagel 60 (a particle size corresponding to 230-400 mesh ASTM). The eluent was a mixture of one part by volume of ethyl acetate and four parts by volume of hexane.

The elemental analysis of the purified product having a molecular weight of 975,45 and the formula $C_{61}H_{98}O_9$ gave the following results:

calculated: C=75,11; H=10,13: found: C=75,12; H=10,13.

The IR spectrum in carbon tetrachloride showed peaks at 1730 aryl-COO, st.) and 1670 (aryl-CO-aryl, st.).

The viscosity of the liquid benzophenonetetracarboxylate at a temperature of 22° C. was 902,5 cP.

EXAMPLE 2

A benzophenonetetracarboxylate correspnding to the formula I stated in example 1 was prepared, however in said ester each of the radicals R, $R_1$, $R_2$ and $R_3$ was a straight chain alkyl radical having 6 carbon atoms.

The preparation of said tetraester was performed according to the method described in example 1, however instead of the undecane-1-ol an equivalent amount of the hexane-1-ol was used.

EXAMPLE 3

Preparation of inventive membranes and a membrane for comparison

According to the present example inventive shaped bodies, i.e. membranes, were prepared by using as plastic material polyvinylchloride and as elastifying component the benzophenonetetracarboxylate prepared according to example 1.

The membranes were prepared by dissolving the appropriate amount of the polyvinylchloride and of the benzophenonetetracarboxylate in a sufficient amount of tetrahydrofurane to yield a clear solution. Said solution was casted to a membrane and after the solvent was evaporated the thickness of said membrane was 100 μm.

Several membranes containing different amounts of the benzophenonetetracarboxylate were prepared. The composition of said membrane, i.e. the % by weight of polyvinylchloride and of elastifier therein contained are stated in the following table:

| membrane | parts by weight of polyvinylchloride | parts by weight of the benzophenonetetra-carboxylate |
|---|---|---|
| A | 10 | 90 |
| B | 30 | 70 |
| C | 40 | 60 |
| C | 54 | 46 |

The membranes A, B and C are examples for inventive membranes, while the membrane D is a membrane for comparison. Said membrane D contains per 10 parts by weight of the polyvinylchloride less than 12 parts by weight of the benzophenonetetracarboxylate and said foil accordingly is outside the scope of the present invention.

Each of the foils A, B, C and D was tested with regard to its adherence on different kinds of substrates like glass, quartz-glass (fused silica) and plexiglass. Onto each of the tested substrates each of the tested foils was applied by pressing it onto the substrate in a slightly stretched or extended condition.

Each of the foils A, B, C and D adhered after the application of each of the tested substrates. If, however, thereafter the area was rubbed with the finger onto which the foils had been adhered, then after the rubbing the foils A, B and C remained firmly adhered to the substrate while said rubbing removed the foil for comparison D from each of the tested substrates.

Using a knife, however, each of the tested foils A, B, C and D could be scratched away from each of the tested substrates. Accordingly, inventive foils can be again removed from a substrate when this is desired. The foils, however, remain firmly adhered to the substrate if the correspondingly coated substrate is handled.

With regard to the tearing strength or breaking strength of all the foils tested in the present test, the foil B showed the best results.

EXAMPLE 4

In this example the washing out or leaching out of prior art plasticizers and of the the inventive elastifying benzophenonetetracarboxylates was tested.

The tested plastic material was a polyvinylchloride of high molecular weight which had been obtained from the Fluka AG, 9470 Buchs, Switzerland.

Each of the tested foils contained 30% by weight, referred to the total weight of the foil, of the polyvinylchloride, and 70% by weight, referred to the total weight of the foil of the plasticizer or the elastifying component respectively.

The following foils I, II, III and IV were prepared which contained the corresponding elastifying components respectively plasticizers.

FOIL I:

The foil contained the benzophenone-tetracarboxylic acid-tetra-n-undecylester prepared according to example 1 as elastifying component. Said elastifying component will be abbreviated in the future as BT-11 and the foil in question accordingly is an example of an inventive shaped body.

FOIL II:

Said foil contained the benzophenone-tetracarboxylic acid-tetra-n-hexal-ester prepared according to example 2. Said elastifying component will be abbreviated in the future as BT-6. Said foil accordingly is an example for an inventive shaped body.

FOIL III:

Said foil contained the sebacinic acid dioctylester, i.e. the dioctyl-sebacate, as plasticizer and said plasticizer will be abbreviated in the future as DOS. Said foil accordingly is an example for a shaped body for comparison.

FOIL IV:

Said foil contained as plasticizer the ortho-nitrophenyl-octylether, which will be abbreviated in the future as o-NPOE. Said foil accordingly is an example of a shaped body for comparison.

In the foils for comparison III and IV frequently used plasticizers were used as elastifying agents in the same amount in which the inventive foils contained the benzophenonetetracarboxylates. The plasticizers of the foils III and IV are usually used as plasticizers of ion sensitive membranes for the determination of the concentrations of ions and said ion sensitive membranes contain in addition to the plastic material and the plasticizer the ion selective component or the cation or anion to be determined.

Each of the membranes I, II, III and IV was put into an aqueous albumin solution which contained per 1 of the solution 70 g of albumin. In each case such a quantity of the albumin solution was used that per each part of volume of the foil 1000 parts of volume of the albumin solution were present.

Each of the tested foils had a thickness of 100 μm and the foils were left for 5 days in the albumin solution at room temperature and during the tests the samples were shaken using a shaking machine.

After said tests the foils were washed with water and thereafter analyzed for their content of the plasticizer or elastifying component in question.

The quantity of plasticizer, respectively elastifying component, each foil contained before the treatment with the albumin solution, i.e. the content of 70%, referred to the total weight of the foil, was stated to be the original content of plasticizer i.e. as 100% plasticizer. In the following table there are stated the percentages of each plasticizer, respectively elastifying component, referred to the originally present 100% of said component in the foil.

| tested foil | % of the originally present plasticizer which was still present in the foil after the treatment with the solution |
|---|---|
| I | 99,8 |
| II | 98,5 |
| III | 70,5 |

| tested foil | % of the originally present plasticizer which was still present in the foil after the treatment with the solution |
|---|---|
| IV | 43,9 |

It can be seen from the results of said table that in the inventive foils the elastifying component was nearly not washed out by the aqueous solution, i.e. only 0,2% and 1,5% of the total amount of the elastifying component were washed out with the albumin solution. The test, furthermore, shows that the benzophenonetetracarboxylate of formula I in which each of the radicals R, $R_1$, $R_2$ and $R_3$ comprises 11 carbon atoms, is leached out to a still lower level than the elastifying components for formula I in which each of the radicals R, $R_1$, $R_2$ and $R_3$ is a straight aliphatic chain comprising only 6 carbon atoms.

Contrary to this the prior art plasticizers were washed out from the foil under identical test conditions in an amount of about 30% by weight or even an amount of more than 50% by weight, always referred to the weight of the plasticizer which had originally been present in the foils.

EXAMPLE 5

In said example the inventive foil I according to the preceding example 4 and also the foil for comparison III according to the preceding example 4 were tested with regard to the migration of the elastifying component, respectively plasticizer in said foil.

Said test was performed by contacting the inventive foil I and also the foils for comparison III with commercially available polyvinylchloride tubes. Said polyvinylchloride tubes were far thicker than the tested foils. Said polyvinylchloride tubings had been used for preparing ion selective electrodes of the catheter-type in which the ion selective membranes are cast onto said polyvinylchloride tubings or sealed onto said polyvinylchloride tubings which are the carriers for said ion selective membranes. Prior art catheder-type electrodes of said kind suffered from mutual migration of the plasticizers of the tubing and the plasticizers of the membrane and this resulted in a rapid deterioration of the electromotive performance of said catheder-type electrodes.

The polyvinylchloride tubing contained 36,6% by weight, referred to the total weight of the tubing, of the plasticizer diethylhexylphthalat, and said plasticizer will be abbreviated in the following as DEHP, and the polyvinylchloride tubing furthermore contained 73,4% by weight, referred to the total weight of the tubing, of polyvinylchloride.

In said test the foil I and the foil III respectively were pressed onto the polyvinylchloride tubing and the foils adhered onto said tubing. After a certain time of adherence the foils were removed from the polyvinylchloride tubing and the migration of the elastifying component from the foil into the tubing, respectively the plasticizer from the tubing into the foil was determined.

Said test showed that after a time of contact of 9480 minutes from the inventive foils I only an extremely low migration of the plastifying component BT-11 of the foils into the polyvinylchloride tubing had occurred. Furthermore after said long test period also only an extremely small migration of the plasticizer DEHP of the polyvinylchloride tubing into the foil had occurred.

Contrary to this the corresponding tests of the foils for comparison III showed that already after a contact time of only 237 minutes a migration of the plasticizer DOS of the foil into the polyvinylchloride tubing could be detected and also the migration of the plasticizer DEHP of the polyvinylchloride tubing into the foil was detected after said short test period.

What is claimed is:

1. A shaped body of plastic material having a high elasticity and high adhesive characteristics which shaped body contains per 10 parts by weight of a plastic material, 7 parts by weight to 90 parts by weight of an elastifying component comprising a benzophenonetetracarboxylic acid tetraester, the alcohol moieties of which tetraester are selected from the group consisting of alkanols having 4–24 carbon atoms, alkenols having 4–24 carbon atoms, and alkynols having 4–24 carbon atoms, and wherein in said tetraester the phenyl nuclei and alcohol moieties are either unsubstituted or substituted with nonionic substituents, with the provision that if the plastic material of said shaped body contains a vinyl chloride homopolymer or vinyl chloride copolymer, there must be present per 10 parts by weight of said plastic material at least 15 parts by weight of the benzophenonetetracarboxylic acid tetraester.

2. A shaped body of plastic material according to claim 1 wherein the alcohol component of the benzophenonetetracarboxylate is a straight chain alcohol or a branched chain alcohol having a single branch only which extends from the main chain.

3. A shaped body according to claim 1, which shaped body has a form selected from the group of forms consisting of a membrane, a foil, a film, a fiber, a strand and a filament.

4. A shaped body according to claim 3 which is an ion sensitive membrane for the determination of the concentration of ions, which ion sensitive membrane further contains an ion sensitive component for the cation or anion concentration to be determined.

5. A shaped body according to claim 1 wherein there are bonded two ester groups to each of the benzene nuclei in the benzophenonetetracarboxylic acid tetraester.

6. A shaped body according to claim 5 wherein the position of each of the two ester groups on one of said benzene nuclei is identical to the position of each of the two ester groups on the other benzene nucleus.

7. A shaped body according to claim 6 wherein the benzophenonetetracarboxylic acid tetraester has the following formula, $$\begin{array}{c}R_2-O-\overset{O}{\underset{\|}{C}}\phantom{xx}\overset{O}{\underset{\|}{C}}\phantom{xx}\overset{O}{\underset{\|}{C}}-O-R\\R_3-O-\underset{\|}{C}\phantom{xxxxxxxxxxxxxxxx}\underset{\|}{C}-O-R_1\\O\phantom{xxxxxxxxxxxxxxxxxxxx}O\end{array}$$

wherein each of R, $R_1$, $R_2$ and $R_3$ are selected from the group consisting of alkyl radicals, alkenyl radicals and alkinyl radicals having 4–22 carbon atoms.

8. A shaped body according to claim 7 wherein R, $R_1$, $R_2$ and $R_3$ are straight chain radicals.

9. A shaped body according to claim 7 wherein R, $R_1$, $R_2$, and $R_3$ are branched chain radicals wherein only a single branch extends from the main chain.

10. A shaped body according to claim 7 wherein R, $R_1$, $R_2$, and $R_3$ are selected from the group consisting of alkyl, alkenyl and alkinyl radicals having 6–20 carbon atoms.

11. A shaped body according to claim 10 wherein R, $R_1$, $R_2$, and $R_3$ are the same.

12. A shaped body according to claim 1 wherein the plastic material is selected from the group consisting of polyethylene, polypropylene, polyvinylchloride, polystyrene, polyester, polyamide, polyacrylnitrile, polyurethane, polycarbonate, polyvinylidene chloride and copolymers thereof comprising at least two different monomeric units, and copolymers in which minor quantities of the monomeric units of said copolymer are derived from hydrophilic monomers.

13. A shaped body according to claim 7 wherein the plastic material is selected from the group consisting of polyethylene, polypropylene, polyvinylchloride, polystyrene, polyester, polyamide, polyacrylnitrile, polyurethane, polycarbonate, polyvinylidene chloride and copolymers thereof comprising at least two different monomeric units, and copolymers in which minor quantities of the monomeric units of said copolymer are derived from hydrophilic monomers.

14. A shaped body according to claim 12 wherein the plastic material is selected from the group consisting of vinyl chloride homopolymers and vinyl chloride copolymers wherein per 10 parts by weight of said polyvinylchloride there are present 15–90 parts by weight of the benzophenonetetracarboxylic acid tetraester.

15. A shaped body according to claim 14 wherein there is present 20–70 parts by weight of the benzophenonetetracarboxylic acid tetraester.

16. A shaped body according to claim 13 wherein the plastic material is selected from the group consisting of vinyl chloride homopolymers and vinyl chloride copolymers wherein per 10 parts by weight of said polyvinylchloride there are present 15–90 parts by weight of the benzophenonetetracarboxylic acid tetraester.

17. A shaped body according to claim 16 wherein there is present 20–70 parts by weight of the benzophenonetetracarboxylic acid tetraester.

18. A shaped body according to claim 4 wherein the ion sensitive membrane comprises 10 parts by weight of polyvinyl chloride, 15–90 parts by weight of the benzophenonetetracarboxylic acid tetraester and 0.1–1 parts by weight of the ion selective component.

19. A shaped body according to claim 18 containing 20–70 parts by weight of the benzophenonetetracarboxylic acid tetraester.

* * * * *